United States Patent [19]

Wynn

[11] 4,160,914
[45] Jul. 10, 1979

[54] APPARATUS FOR MEASURING OF PARTICULATE SCATTERING IN FLUIDS

[75] Inventor: William H. Wynn, Hillsborough, Calif.

[73] Assignee: Monitek, Inc., Redwood City, Calif.

[21] Appl. No.: 861,218

[22] Filed: Dec. 16, 1977

[51] Int. Cl.² ........................................... G01N 21/26
[52] U.S. Cl. ............................... 250/574; 250/237 R; 250/239; 356/339
[58] Field of Search ................... 250/237 R, 239, 573, 250/574; 340/628, 630; 356/103, 104

[56] References Cited

U.S. PATENT DOCUMENTS

| | | | |
|---|---|---|---|
| 1,449,512 | 3/1923 | Ives | 250/237 R X |
| 2,033,466 | 3/1936 | Grant | 340/630 X |
| 3,170,068 | 2/1965 | Petriw et al. | 250/237 R X |

Primary Examiner—James B. Mullins
Attorney, Agent, or Firm—Lowhurst & Aine

[57] ABSTRACT

An apparatus for the measurement of particulate scattering in fluids which is particularly suitable for low particulate concentration. The apparatus includes a housing with a cuvette for confining the fluid containing the particulate to be measured placed substantially at the center of the housing. A collimated light source provides a beam directed along an axis for illuminating the contents of the cuvette, and a light sensitive detector for receiving light scattered due to particulates along a selected axis. Surrounding the detector are a pair of equidistantly spaced baffles, of cylindrical or spherical configuration, which have a pair of aligned apertures centered about the scattering axis, and nonreflective facing surfaces.

17 Claims, 3 Drawing Figures

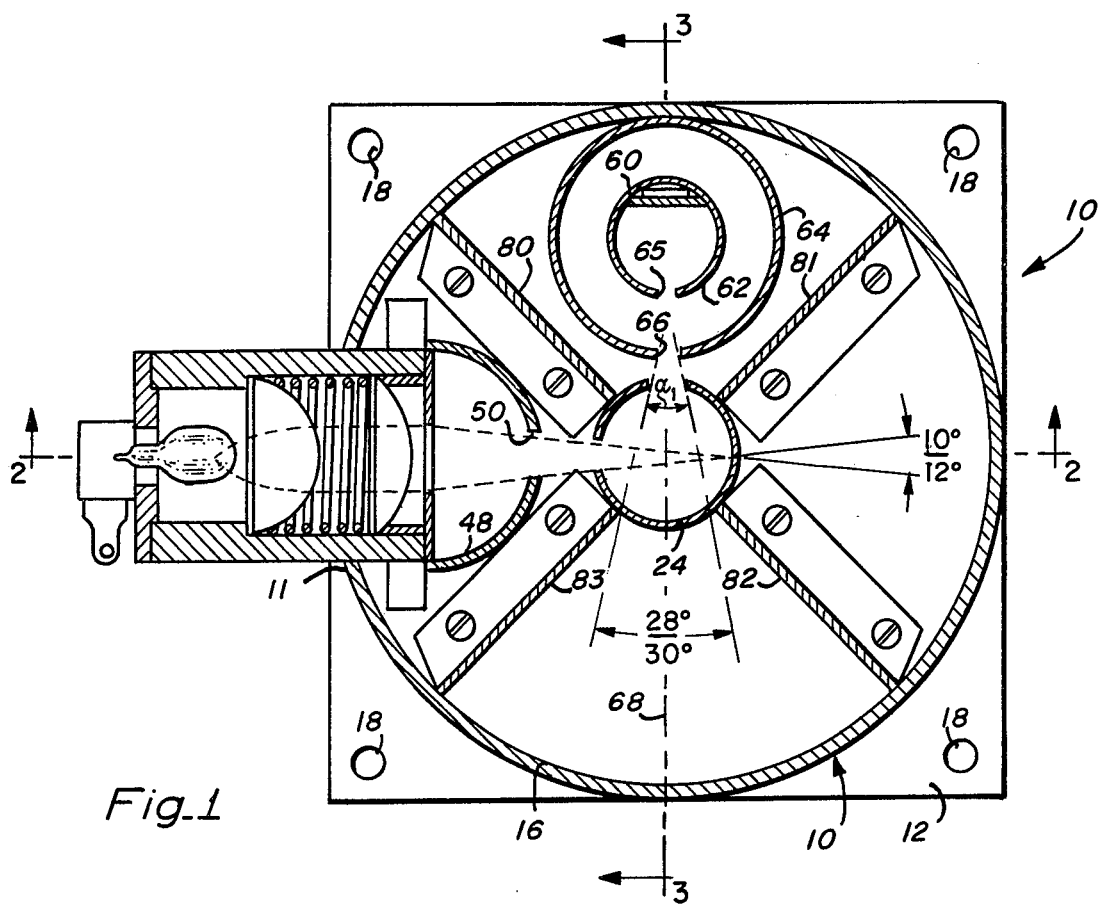
Fig_1
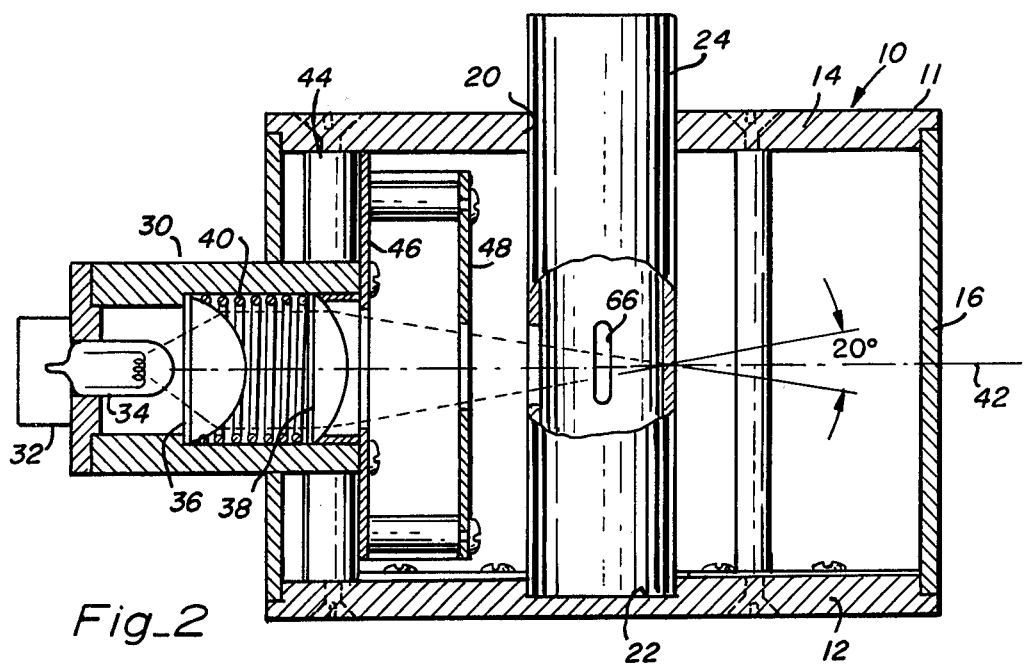
Fig_2

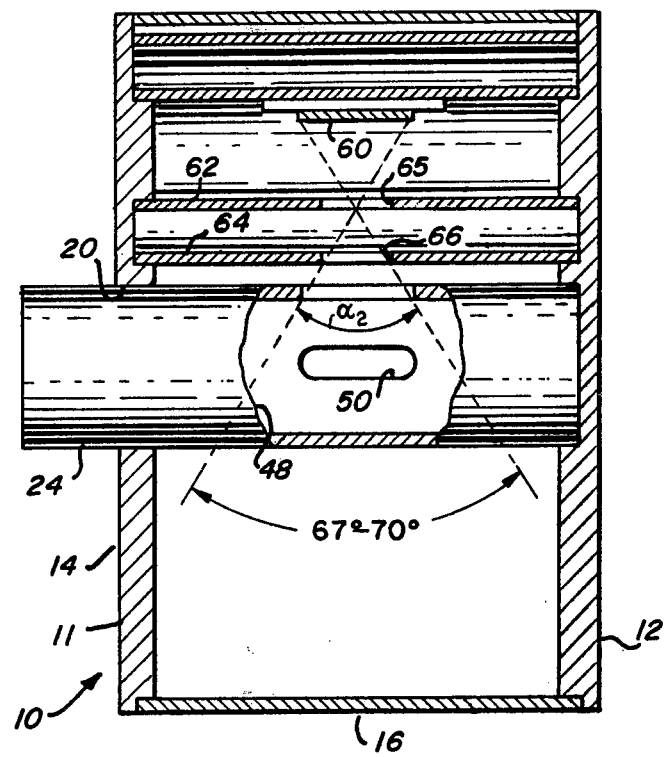
Fig_3

APPARATUS FOR MEASURING OF PARTICULATE SCATTERING IN FLUIDS

BACKGROUND OF THE INVENTION

This invention relates to an apparatus for the measurement of light scattered by a particulate within a fluid, and more particularly to a turbidity meter that measures the amount of suspended solids or contaminate in the fluid, particularly for low and very low concentrations of particulate.

Turbidity meters are in wide use today to determine or to indicate the cleanliness of a liquid or a gas by measuring the amount of contaminants therein which are usually in the form of suspended solids. Turbidity meters, such as those to which this invention relates, are not only in common use today for the control of industrial processes, such as determining the cleanliness of gasoline during the refining process, but are also being used for ecological controls, such as measuring the cleanliness of smoke that is allowed to escape from an industrial smoke stack.

As described in U.S. Pat. No. 3,510,666 to Topol, there are basically two types of turbidity meters, one which uses the amount of directly transmitted light and the other which uses the amount of scattered light, either forward or at some selected angle. Utilization of the directly transmitted light involves a light detector which measures the amount of light that is received after transmission through the fluid, and the less transmitted light is received by the detector, the greater is the turbidity. When the turbidity is very low, the light received by the detector is very much the same as the light transmitted, and when the turbidity is very high, the light received by the detector is only a small fraction of the light transmitted. This method has been found unsuitable for the measurement of low particulate concentration because the transmitted and received light are almost equal and therefore the sensitivity is very low. The same is true for high concentrations where hardly any light is received.

The scattered light method has a light sensitive detector positioned along any axis on which scattering is to be measured and which is shielded from the direct light transmitted along a transmission axis in case the forward scattered light is to be measured. The light measured is actually the light that is scattered by the particulate, and as the concentration of the particulate increases, the amount of scattered light likewise increases until the concentration becomes so high that intervening particles make the measure difficult because there would be secondary scattering. This method is preferred for low particulate concentration.

One of the difficulties with scattering type turbidity meters of the prior art, particularly if the particulate concentration is low, has been their sensitivity to light signals other than those due to scattering, such as internal reflections of the illuminating beam of light and ambient light which could reach the detector. When the particulate concentration is very low, say from 0.1 to 100 Formazin units, the error signals due to internal reflection and to ambient lighting have been found to be approximately of the same order of magnitude as the scattered light, which therefore causes substantial errors.

SUMMARY OF THE INVENTION

It is therefore an object of the present invention to provide an improved turbidity meter which utilizes scattered light and which is relatively insensitive to either internal reflections or to ambient light.

It is another object of the present invention to provide an improved turbidity meter that is particularly suited for measuring the turbidity when the particulate concentration is low or very low, say in the range of 0.1 to 100 Formazin units, and which provides accurate results relatively free from errors.

It is another object of the present invention to provide an improved turbidity meter having a light sensitive detector which is baffled in such a manner that its angle of acceptance of light is limited to a well defined three dimensional angle of acceptance about a central axis, and which is substantially insensitive to any light having a direction which lies outside of the angle of acceptance.

It is another object of the present invention to provide a light sensitive detector and a baffle means surrounding the detector with the baffle means being designed to provide a detector acceptance angle which is selected in accordance with certain criteria and which makes the detector output insensitive to any light which has a direction lying outside of the acceptance angle of the detector.

Briefly, these and other objects are achieved in accordance with the present invention by providing a housing, preferably of cylindrical shape, having a container or cuvette at the center thereof for housing the fluid whose turbidity is to be determined. A light source provides a collimated beam for illuminating the sample along an axis of illumination. A light sensitive detector is mounted within the housing with its active surface perpendicular to a selected scattering axis, and is surrounded by a pair of parallel baffles, such as cylinders or spheres, with nonreflective facing surfaces. A pair of apertures of substantially the same configuration and centered about the scattering axis are provided in the baffles, and the dimension of the apertures are selected to define a selected solid angle of acceptance.

BRIEF DESCRIPTION OF THE DRAWINGS

FIG. 1 is a top view, in cross section, of the turbidity meter of the present invention.

FIG. 2 is a cross-sectional view, taken along line 2—2 of FIG. 1; and

FIG. 3 is a cross-sectional view taken along line 3—3 of FIG. 1.

DETAILED DESCRIPTION OF THE INVENTION

Referring now to the drawings, in which like reference characters designate like parts, there is shown an apparatus 10 for measuring particulate scattering in fluids including a housing 11 having a bottom plate 12 and a top plate 14 separated by a cylindrical housing wall 16. Bottom plate 12 and top plate 14 may be bolted to one another across the housing wall by fastening means such as screws 18, or any other convenient method to secure the elements of the housing together. Typically, the size of housing 11 may define an internal chamber about five and one-half inches in diameter and about three inches high.

Top plate 14 is provided with an opening 20 and bottom plate 12 is provided with a well 22 which are dimensioned to accommodate a cuvette 24 inserted into housing 10 through the top plate. Cuvette 24 forms a receptical for holding the fluid whose turbidity is to be measured, and may be replaced by an open tube to allow the on-line monitoring of the turbidity of a fluid.

Housing 10 is further provided with a source of direct illumination 30 which comprises a lamp socket 32 holding a halogen lamp 34. Lamp 34 is covered by aspheric lens 36 which typically has a focal length of 18 millimeters and illuminates a projection lens 38 which typically has a focal length of 32 millimeters for the illustrated housing 11. Lenses 36 and 38 may be held apart by a compression spring 40 which is axially aligned with the optical elements of source 30. The light emanating from source 30 defines an axis of illumination 42 which passes through the center of cuvette 24 and is focused, more or less, on the wall of cuvette 24 most distant to lamp 34. Source 30 is held in cylindrical wall 60 by a source mounting means 44 and the beam of light, collimated by the lens system, is controlled in lateral extent by an aperture plate 46 and a semicylindrical shield 48 having a rectangular aperture 50, also referred to as the illuminating light aperture, which typically is 0.2 inches wide and 0.8 inches long. With the dimensions given, the beam for illuminating the sample makes an angle of approximately 5° with the illumination axis in a horizontal direction and an angle of approximately 10° with respect to the illumination axis in a vertical direction.

There is also provided a light sensitive detector 60, which typically is of the photoelectric, photoconductive or photocurrent kind having an active area of one by two centimeters. Detector 60 is mounted inside an inner baffle 62 having a circular horizontal cross section, which in turn is mounted inside an outer baffle 64 which likewise has a circular horizontal cross section. Inner baffle 62 and outer baffle 64, which together form a baffle means, are spaced parallel to one another and are provided, respectively, with apertures 65 and 66, also referred to as scattering light apertures, which are typically 0.1 inch in width and 0.8 inch in length and which are symmetric with respect to a selected scattering axis 68. Even though inner baffle 62 and outer baffle 64 are shown in the form of cylinders, extending from bottom plate 12 to to plate 14, it should be understood that they could likewise be spherical in extent in which case the scattering light aperture would be selected to be circular. Further, the surfaces of baffles 62 and 64 facing one another are provided with an antireflective surface for reasons that will become clear hereinafter.

The size of apertures 65 and 66, as well as their separation, i.e., the distance between baffles 62 and 64, are important and are selected so that only light from selected directions can fall on the active detector surface. For the purpose of this application, the solid formed the using the direction of light at the border between acceptance and nonacceptance as a generatrix line is referred to as the solid angle of acceptance which would be a cone (surface of revolution) in the case of circular apertures and a triangular prism in case of rectangular apertures. In case of a rectangular aperture with rounded ends, the solid angle of acceptance will be a triangular prism with the distant smaller faces being semiconical.

In the illustrated baffle means, the spacing between baffles is selected so that the angle of acceptance in the horizontal plane, namely $\alpha_1$ as shown in FIG. 1, is about 15° with the scattering axes, and the angle of acceptance in the vertical plane, namely $\alpha_2$ as shown in FIG. 3, is about 35° with the scattering axes and is limited by the height (lateral extent) of the active area of the detector. The angle of acceptance in the illustrated baffle is defined in each plane by drawing two lines each of which extends, respectively, from one wall of one aperture of one baffle to the opposite wall of the aperture of the other baffle as shown in FIG. 1 and 3. As long as these lines intersect detector 60 within the active area, the angle which these lines make with one another is the angle of acceptance in the applicable plane. In the case of the longitudinal angle of acceptance, as illustrated in FIG. 1, the two lines intersect the active area of the detector and therefore define the angle of acceptance $\alpha_1$, which is 30°, or 15° to either side of the scattering axis. In case of the vertical angle of acceptance $\alpha_2$, as illustrated in FIG. 3, the two lines, if drawn to the opposite wall of the other baffle aperture would not intersect the sensitive area of detector 60. Therefore, the lines are drawn from opposite walls of the aperture of the end baffle to the end of the active detector area to now define the angle of acceptance which is illustrated as 70° or 35° to either side of the scattering area.

Referring now particular to FIG. 3 of the drawing, it is seen from an inspection thereof that the vertical angle of acceptance of approximately 70° was carefully selected so that no ambient light beam opening 20, falling into housing 10, would reach detector 60. Likewise, the horizontal angle of acceptance was selected in such a manner that few, if any, of the reflections which may be generated by the direct light beam would be within the solid angle of acceptance. The rule adopted is that both the horizontal and vertical angle of acceptance are made as large as possible, for maximum sensitivity, as is consistent with rejecting ambient lighting particularly in the vertical direction and minimizing reflected light from the direct beam particularly in the vertical direction.

In order to further assure against any reflection, from the direct beam of light from source 30, from reaching detector 60, there are provided a number of baffles 80, 81, 82 and 83 of which 80 is the most important. All surfaces inside housing 10 are coated or are made nonreflective to further cut down reflection.

The parallel double baffle around detector 60 has been found particularly efficient in defining a sharp solid angle of acceptance which efficiently rejects any and all light reaching the baffles at an angle which is outside of the solid angle of acceptance. Any light that may pass through aperture 66 is intercepted by the nonreflective outer surface of baffle 62 and is reflected from that surface to the inner surface of baffle 64, and so on until the light is completely absorbed.

The output of detector 60 is utilized in the manner well-known in the art to provide a current which is then converted into an electrical indication of the amount of light scattered along the scattering axes. Also, even though detector 60 has been shown to be at right angles to the axis of illumination 42, it is to be understood that such a detector can be placed at any angle with respect to the axis of illumination 42, even at a very small angle to measure forward scattering or at an angle almost immediately adjacent to source 30 to measure back scattering.

There has been described an apparatus for measuring particulate scattering in a fluid which is particularly efficient when the particulate concentration is low or very low. The disclosed apparatus is remarkably insensitive to ambient light and reflected light providing the baffle means is designed to have a solid angle of acceptance to discriminate against such light sources of error.

What is claimed is:

1. An optical apparatus for the measurement of light scattered by a particulate within a fluid in the direction of a scattering axis, comprising:
   a housing;
   a tubular enclosure confining the fluid with the particulate, having at least an optically transparent portion, disposed in said housing;
   a light source for emitting light in the direction of an illumination axis into said housing and through said optically transparent portion;
   a light sensitive detector having an active area which is disposed within said housing at right angles to and centrally with the scattering axis;
   a first battle surrounding said detector, said first baffle having a first aperture centered about said scattering axis;
   a second baffle, identical in shape to but larger than said first baffle, surrounding said first baffle and being equidistantly spaced therefrom, said second baffle having a second aperture centered about said scattering axis;
   the shape and size of said first and second apertures and the lateral extent of said active area being selected so that a line generatrix touching the wall of said second aperture and passing through said first aperture and intersecting said active area generates a solid surface defining a predetermined solid angle of acceptance within which light will reach said detector.

2. An optical apparatus for the measurement of light in accordance with claim 1 in which the line generatrix, while touching the wall of said second aperture, follows the edge of said active area.

3. An optical apparatus for the measurement of light in accordance with claim 1 in which said predetermined solid angle of acceptance is selected so that any light entering the housing through access openings is lying outside of the solid angle of acceptance.

4. An optical apparatus for the measurement of light in accordance with claim 1 in which the housing configuration and the access ports into the housing are selected to lie outside of the predetermined solid angle of acceptance so that ambient light entering through access ports does not reach said detector.

5. An optical apparatus in accordance with claim 1 in which said first and second baffles are cylindrical in shape.

6. An optical apparatus in accordance with claim 1 in which said first and second baffles are spherical in shape.

7. An optical apparatus in accordance with claim 1 in which at least the exterior surface of said first baffle is nonreflective.

8. An optical apparatus in accordance with claim 1 in which at least the interior surface of said second baffle is nonreflective.

9. An optical apparatus in accordance with claim 1 in which at least the interior surface of said firt baffle and the exterior surface of said second baffle are nonreflective.

10. An optical apparatus for the measurement of light in accordance with claim 1 in which the line generatrix while touching the wall of said second aperture, also touches the opposite wall of said first aperture.

11. A light sensitive detector means having a preselected solid angle of acceptance of light about an acceptance axis and a high degree of rejection of light lying outside the angle of acceptance, the detector means comprising:
    a photoelectric detector having an active area substantially at right angles to the acceptance axis;
    a first baffle surrounding said detector, said first baffle including a first aperture centered about the acceptance axis;
    a second baffle, identical in shape to but larger than said first baffle, surrounding said first baffle and being equidistantly spaced therefrom, said second baffle including a second aperture also centered about the acceptance axis;
    the relative shape and size of said active area, said first aperture and said second aperture being selected so that a line generatrix lying in a common plane with the acceptance axis and connecting the wall of said second aperture with the opposite wall of said first aperture generates the predetermined solid angle of acceptance.

12. A light sensitive detector means as recited in claim 11 in which the lateral extent of said active area is selected so that said line generatrix is constantly intersecting said active area.

13. A light sensitive detector means as recited in claim 11 in which said first and second baffles are cylindrical in shape.

14. A light sensitive detector means as recited in claim 11 in which said first and second baffles are spherical in shape.

15. A light sensitive detector means as recited in claim 11 in which at least the exterior surface of said first baffle is nonreflective.

16. A light sensitive detector means as recited in claim 11 in which at least the interior surface of said second baffle is nonreflective.

17. A light sensitive detector means as recited in claim 11 in which at least the interior surface of said first baffle and the exterior surface of said second baffle are nonreflective.

* * * * *

UNITED STATES PATENT AND TRADEMARK OFFICE
CERTIFICATE OF CORRECTION

PATENT NO. : 4,160,914
DATED : July 10, 1979
INVENTOR(S) : William H. Wynn

It is certified that error appears in the above-identified patent and that said Letters Patent are hereby corrected as shown below:

Column 3, line 59; change "triangular" to "rectangular"

Column 3, line 61; change "triangular" to "rectangular"

Signed and Sealed this

Eighth Day of June 1982

[SEAL]

Attest:

Attesting Officer

GERALD J. MOSSINGHOFF
Commissioner of Patents and Trademarks